(12) United States Patent
Yang

(10) Patent No.: US 8,541,558 B2
(45) Date of Patent: Sep. 24, 2013

(54) FLUORESCENT PROTEINS AND USES THEREOF

(75) Inventor: Jenny J. Yang, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 2005 days.

(21) Appl. No.: 11/381,495

(22) Filed: May 3, 2006

(65) Prior Publication Data

US 2009/0035783 A1     Feb. 5, 2009

Related U.S. Application Data

(60) Provisional application No. 60/677,286, filed on May 3, 2005.

(51) Int. Cl.
| | |
|---|---|
| *C07H 21/04* | (2006.01) |
| *G01N 33/53* | (2006.01) |
| *C12P 21/06* | (2006.01) |
| *C12N 1/20* | (2006.01) |
| *C12N 15/00* | (2006.01) |

(52) U.S. Cl.
USPC ....... 536/23.1; 435/7.1; 435/69.1; 435/252.3; 435/320.1

(58) Field of Classification Search
None
See application file for complete search history.

(56) References Cited

U.S. PATENT DOCUMENTS 7,001,986 B2 * 2/2006 Bjorn et al. .................. 530/350
2004/0137528 A1 7/2004 Watson Michnick et al.

FOREIGN PATENT DOCUMENTS

EP     1209167 A1     5/2002
WO     99/64592     12/1999

OTHER PUBLICATIONS

David P. Barondeau, Elizabeth D. Getzoff; Structural insights into protein-metal ion partnerships; Current Opinion in Structural Biology 2004, 14:765-774.
Yi Lu; Design and engineering of metalloproteins containing unnatural amino acids or non-native metal-containing cofactors; Current Opinion in Structural Biology 2005, 9:118-126.
Thomas J. Magliery, et al.; Detecting Protein—Protein Interactions with a Green Fluorescent Protein Fragment Reassbmly Trap: Scope and Mechanism; J. AM. Chem. Soc. 2005, 127, 146-157.
Takeaki Ozawa, et al.; A Genetic approach to identifying mitochondrial proteins; Nature Biotechnology, Mar. 2003, vol. 21, p. 287-293.
Takeaki Ozawa, et al.; A high-throughput screening of genes that encode proteins transported into the endoplasmic reticulum in mammalian cells; Necleic Acids Research, 2005, vol. 33, No. 4 p. 1-9.
Supplemental European Search Report, 2009.
Remy, Ingrid and Michnick, Stephen W., "A cDNA Library Functional Screening Strategy Based on Fluorescent Protein Complementation Assays to Identify Novel Components of Signaling Pathways," www.sciencedirect.com, Mathods 32 (2004) 381-388.
Chen, et al., "Designing Protease Sensors for Real-time Imaging of Trypsin Activation in Pancreatic Cancer cells," Biochemistry, 2-26, ACS Paragon Plus Environment, 2008.
XP-002519893. pp. 1-2, 2007.

* cited by examiner

*Primary Examiner* — Tekchand Saidha
*Assistant Examiner* — Md. Younus Meah
(74) *Attorney, Agent, or Firm* — Thomas Horstemeyer, LLP

(57) ABSTRACT

A fluorescent sensor and methods for producing and using the fluorescent sensor. Such fluorescent sensors have broad applicability in characterizing cells and organisms, in detecting or measuring various cellular parameters, and in detecting or measuring protein-protein/peptide interactions.

16 Claims, 8 Drawing Sheets

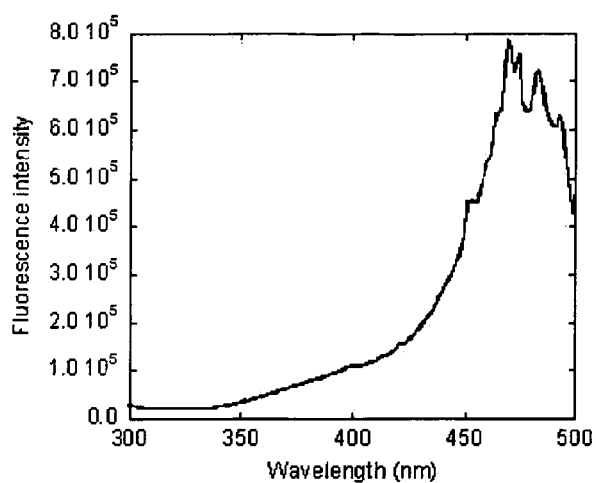 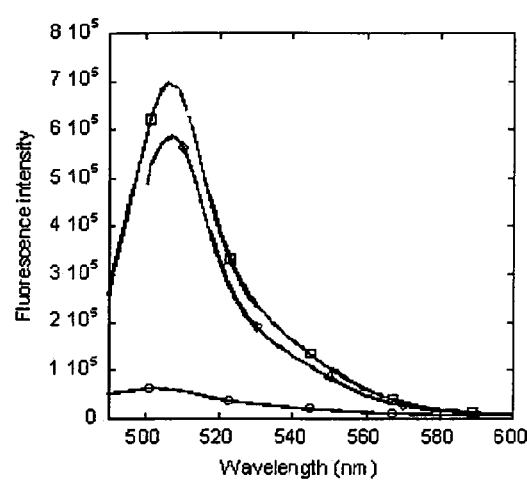
FIG. 4          FIG. 5

FLUORESCENT PROTEINS AND USES THEREOF

STATEMENT OF RELATED APPLICATIONS

This application claims priority on U.S. Provisional Patent Application No. 60/677,286 entitled "Fluorescent Protein and Uses Thereof" having a filing date of 3 May 2005, which is hereby incorporated by reference.

BACKGROUND OF THE INVENTION

1. Technical Field

This invention is related generally to the field of molecular and cellular biology. More particularly, this invention is related to fluorescent proteins and to methods for the preparation and use thereof.

2. Prior Art

*Aequorea* green fluorescent proteins (GFPs) have 238 amino acid residues in a single polypeptide chain. The native molecule has been shown to regenerate its intrinsic fluorescence from the totally denatured state. GFPs display a strong visible absorbance and fluorescence is thought to be generated by the autocyclization and oxidation of the chromophore having a tripeptide Ser-Tyr-Gly sequence at positions 65 to 67. Mutations to GFPs have resulted in various shifts in absorbance and fluorescence. The usefulness of GFPs stems from the fact that fluorescence from GFP requires no additional co-factors; the fluorophore is self-assembling via a cyclization reaction of the peptide backbone.

The chromophore of GFP is formed by the cyclization of the tripeptide Ser65-Tyr66-Gly67. This chromophore is located inside of the β-barrel that is composed of 11 anti-parallel strands and a single central α-helix. There are short helices capping the ends of the β-barrel. The chromophore has extensive hydrogen bonding with protein frame and can be affected by water molecules under the different folding status. The chromophore in a tightly constructed β-barrel exhibits absorption peaks at 400 and 480 nm and an emission peak at 510 nm with a quantum yield of about 0.72 when excited at 470 nm. The chromophore in enhanced green fluorescent protein (EGFP), which is GFP with a mutation S65T, has an improved fluorescence intensity and thermo-sensitivity.

Yellow fluorescent protein (YFP: S65G, V68L, S73A, T203Y), cyanide fluorescent protein (CFP: Y66W, N146I, M152T, V163A, N212K), and blue green fluorescent protein (BFP: Y66H, Y145F) are variants of GFP that differ in emission spectra and emission. Further, additional GFP variants, such as Venus, also have been constructed to have accelerated maturation and brightness. Due to the overlapping emission spectra and excitation spectra of GFP variants, fluorescence resonance energy transfer (FRET) from one to the other variants can be observed when the variants are in close proximity.

As GFPs may be cloned and expressed in a range of vectors across a diverse range of cells and organisms, GFPs are versatile tools for monitoring and visualizing physiological processes, protein localization, and expression of genes. GFPs are bio-compatible, and when used as a tag do not alter the normal function or localization of a protein to which they are fused. Proteins, cells and organelles marked with GFPs can be visualized and monitored in living tissue without the need for fixation. As such, it is possible to use GFPs to monitor and quantify the dynamics of cellular processes non-invasively in real time.

Accordingly, there is a need for improved fluorescent proteins that may be used in both in vivo and in vitro systems. Such fluorescent proteins should be able to detect changes in microenvironments so as to be useful as probes of cellular events involving changes in such microenvironments. Further, such fluorescent proteins should comprise a relatively short amino acid sequence that is relatively shorter than the sequence of natural GFPs, so that they may have applications in studies necessitating small proteins. In addition, the fluorescence signal of such fluorescent proteins should be able to be enhanced upon interaction with other peptides, proteins, or fragments. Further, there is a need for methods to produce fluorescent proteins exhibiting more efficient chromophore maturation. It is to these needs among others that the present invention is directed.

BRIEF DESCRIPTION OF THE INVENTION

This invention provides a fluorescent protein (termed the fluorescent sensor herein) and methods for producing and using the fluorescent sensor. The nucleic acid sequences and the amino acid sequences encoding the fluorescent sensor are useful for use of the fluorescent sensor as a tool for, for example, monitoring and visualizing physiological processes, protein localization, expression of genes, and protein-protein/peptide interactions.

The fluorescent sensor of this invention can be useful as fluorescent markers in the many ways that such markers are already in use by those of ordinary skill in the art. For, example, such uses include coupling the fluorescent sensor to antibodies, nucleic acids or other receptors for use in detection assays, such as immunoassays or hybridization assays. Further, the fluorescent sensor can be used to track the movement of proteins in cells by expressing the fluorescent sensor in an expression vector. For another example, the fluorescent sensor can be useful in systems to detect induction of transcription.

In one embodiment, the fluorescent sensor can be coupled with a complimentary fragment such as a P10 fragment or a P8 fragment to allow further fluorescence. In this embodiment, the smaller fragment can be expressed in the host cell; once the fluorescent sensor is introduced into the host cell, the fluorescent sensor couples with the smaller fragment to produce different fluorescent characteristics. The fluorescent sensor may be introduced into a host cell by direct delivery to the cell or may be expressed by the host cell, e.g., by a vector. In addition, both protein fragments expressed in bacteria, mammalian and in vitro systems can be used directly to monitor the interactions with fused partners in cell lysates, at the extracellular spaces, or tissue samples. They can be very useful for high throughput screening in drug discovery and identification procedures, and for new target validations of diseases.

The present invention also relates to kits containing one or more compositions of the invention, for example, fluorescent proteins, which can be a portion of a fusion protein, or one or a plurality of polynucleotides that encode the proteins. A kit of the invention also can contain one or a plurality of recombinant nucleic acid molecules, which encode, in part, fluorescent proteins, which can be the same or different, and further can include, for example, an operatively linked second polynucleotide containing or encoding a restriction endonuclease recognition site or a recombinase recognition site, or any polypeptide of interest.

These uses, and other uses, features and advantages of the present invention, will become more apparent to those of ordinary skill in the relevant art when the following detailed description of the preferred embodiments is read in conjunction with the appended figures.

BRIEF DESCRIPTION OF THE FIGURES

FIG. 4 shows the excitation and emission spectra of an example of the fluorescent sensor.

FIG. 5 shows the larger sensor emits a stronger emission peak at about 503 nm when exited with radiation at wavelengths of 398 nm.

DETAILED DESCRIPTION OF THE PREFERRED EMBODIMENTS

1. Definitions

Figure 1:
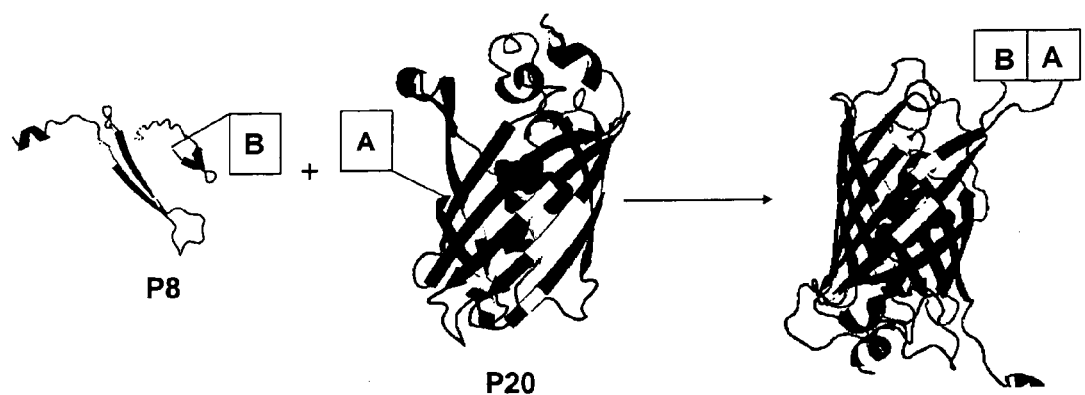
FIG. 1 shows a model structure of an embodiment of the fluorescent sensor fused with a protein of interest.

Unless specifically indicated otherwise, all technical and scientific terms used herein have the same meaning as commonly understood by those of ordinary skill in the art to which this invention belongs. For purposes of the present invention, the following terms are defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. For example, this term can refer to single and double stranded forms of DNA or RNA.

The term "recombinant nucleic acid molecule" refers to a non-naturally occurring polynucleotide containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein linked to a polypeptide of interest. The term "recombinant host cell" refers to a cell that contains or can express a recombinant nucleic acid molecule.

The term "encoding" in the context of a polypeptide refers to the transcription of the polynucleotide and translation of the mRNA produced therefrom. The encoding polynucleotide is considered to include both the coding strand, whose nucleotide sequence can be identical to an mRNA, as well as its complementary strand. It will be recognized that encoding polynucleotides are considered to include degenerate nucleotide sequences, which encode the same amino acid residues. Nucleotide sequences encoding a polypeptide can include polynucleotides containing introns and exons.

The term "control sequences" refer to polynucleotide sequences that are necessary to effect the expression of coding and non-coding sequences. Such control sequences can include a promoter, a ribosomal binding site, and a transcription termination sequence. The term "control sequences" is intended to include, at a minimum, components whose presence can influence expression and can also include additional components whose presence is advantageous. For example, leader sequences and fusion partner sequences are control sequences.

The term "operatively linked" or "operatively joined" or "operatively incorporated" or the like refers to polypeptide sequences that are placed in a physical and functional relationship to each other. In a most preferred embodiment, the functions of the polypeptide components of the chimeric molecule are unchanged compared to the functional activities of the parts in isolation. For example, a fluorescent protein can be fused to a polypeptide of interest and in the fused state retain its fluorescence while the polypeptide of interest retains its original biological activity.

As used herein, the term "brightness," with reference to a fluorescent protein, is measured as the product of the extinction coefficient (EC) at a given wavelength and the fluorescence quantum yield (QY).

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound.

The term "label" refers to a composition that is detectable with or without instrumentation, for example, by visual inspection, spectroscopy, or a photochemical, biochemical, immunochemical or chemical reaction. For example, a label can be phosphorus-32, a fluorescent dye, a fluorescent protein, an electron-dense reagent, an enzyme (such as is commonly used in an ELISA), a small molecule such as biotin, digoxigenin, or other haptens or peptides for an antiserum or antibody. For example, a label can generate a measurable signal such as fluorescent light in a sample.

The term "polypeptide" or "protein" refers to a polymer of two or more amino acid residues. "Polypeptides" or "proteins" are polymers of amino acid residues that are connected through amide bonds. As defined herein, peptides are inclusive of both natural amino acids and unnatural amino acids (e.g. beta-alanine, phenylglycine, and homoarginine). While amino acids are alpha-amino acids, which can be either of the L-optical isomer or the D-optical isomer, the L-optical isomers are preferred. Such amino acids can be commonly encountered amino acids that are not gene-encoded, although preferred amino acids are those that are encodable.

The term "isolated" or "purified" refers to a material that is substantially or essentially free from components that normally accompany the material in its native state in nature. Purity generally can be determined using analytical chemistry techniques such as polyacrylamide gel electrophoresis, high performance liquid chromatography, and the like. A polynucleotide or a polypeptide is considered to be isolated when it is the least predominant species present in a preparation.

The term "naturally-occurring" refers to a protein, nucleic acid molecule, cell, or other material that occurs in nature. A naturally occurring material can be in its form as it exists in nature, and can be modified by the hand of man such that, for example, it is in an isolated form.

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

Two or more amino acid sequences or two or more nucleotide sequences are considered to be "similar" if the amino acid sequences or the nucleotide sequences share at least 50% sequence identity with each other, or with a reference sequence over a given comparison window. Thus, substantially similar sequences include nucleotide sequences considered to be "substantially identical" or "substantially similar".

The term "fluorescent properties" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy.

The term "fluorescent protein" refers to any protein capable of light emission when excited with an appropriate electromagnetic energy. Fluorescent proteins include proteins having amino acid sequences that are either natural or engineered, such as the fluorescent proteins derived from *Aequorea victoria* fluorescent proteins.

The term "mutant" or "variant" also is used herein in reference to a fluorescent protein that contains a mutation with respect to a corresponding wild type fluorescent protein. In addition, reference is made herein to a "spectral variant" or "spectral mutant" of a fluorescent protein to indicate a mutant fluorescent protein that has a different fluorescence characteristic with respect to the corresponding wild type fluorescent protein.

2. Preferred Embodiments

This invention provides nucleic acid sequences and amino acid sequences of a modified green fluorescent protein (GFP) from *Aequorea* green fluorescent proteins, referred to herein as a fluorescent sensor. These nucleic acid sequences and amino acid sequences encoding the fluorescent sensor may be useful for monitoring and visualizing physiological processes, protein localization, and expression of genes. Such fluorescent sensors have broad applicability in characterizing cells and organisms and in detecting or measuring various cellular parameters.

Further, the fluorescent sensor may be used to identify protein binding peptide partners (such as protein-protein or protein-peptide interactions) at the cellular level. More particularly, the sensor can be used to determine peptide partners, even if previously unknown, in bacteria and eukaryotes and can be used to visualize cellular and sub-cellular protein localization in multicellular organisms. The fluorescent sensor also can be used to monitor signaling processes and molecular interactions in conjunction with other fluorescent entities such as other fluorescent proteins via FRET. These uses, along with other typical uses of fluorescent markers, are evident to or are discoverable by one of ordinary skill in the art using ordinary documented research techniques.

FIG. 1 shows a model structure of the fluorescent sensor fused with a protein of interest. As may be seen, the fluorescent sensor with its independent fluorescence properties can be fused with a protein of interest. In a sense, the protein of interest is tagged by the fluorescent sensor. This type of direct link embodiment is the similar to the ordinary use of fluorescent markers.

Figure 2:
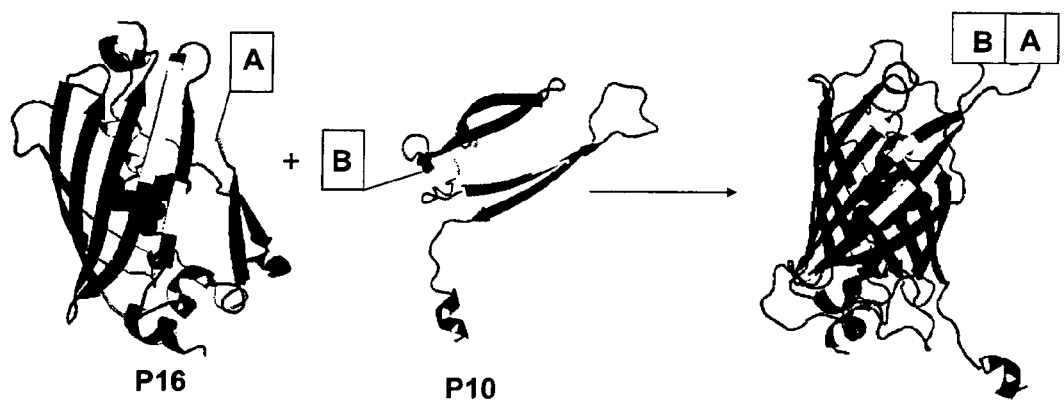
FIG. 2 shows a model structure of another embodiment of the fluorescent sensor fused with a protein of interest.

FIG. 2 shows the model structures of the small fluorescent protein interacting with a complementary fragment and producing a complex with enhanced fluorescence. The fluorescent sensor was able to interact with a complementary fragment to form a complex with enhanced fluorescence. For example, the fluorescent sensor (Sequence Id Nos. 13-16) was able to interact with fragments about 10529 Dalton to emit a stronger signal in, for example, the yellow band. In another example, the fluorescent sensor (Sequence Id. Nos. 9-12) could bind with a protein of about 8000 Daltons with Sequence Id. No. 4 and emit a strong signal at 398 and 498 nm. In a further example, the fluorescent sensor with Sequence Id. No. 13 could bind with a protein of about 10000 Daltons and emit a strong signal at 398 and 498 nm. While the complementary fragments need not show fluorescence, the binding of complimentary fragment to the fluorescent sensor can significantly enhance the signal emitted by the fluorescent sensor. The optical properties, such as absorbance and fluorescence, can be used to quantify the concentration of the sensors in vitro and in vivo. The enhanced fluorescence of the complex can be disparate from the fluorescence of the fluorescent sensor.

The fluorescent protein sensor was created by digesting a modified GFP or variants thereof with enzymes such as trypsin and chymotrypsin. More particularly, the GFP or variants thereof derived from *Aequorea victoria* were first modified by introducing a cleavage sequence at amino acid positions 172-173, 157 and 158, respectively. An exemplary cleavage sequence of Sequence Id. No. 20, which was used to prepare various fluorescent sensors and complementary fragments. With the addition of the protease, the proteins were cleaved at sites between amino acid positions 172-173 and/or 157-158 (b series, for P16K) to yield a novel small fluorescent protein sensor of the present invention. It was found that these sequences could be either cleaved by trypsin or chymotrypsin or a combination thereof.

Sequence Id Nos. 1 through 8 are examples of modified fluorescent proteins that were digested with various enzymes to result in the small fluorescent proteins. Sequence Id. Nos. 1 and 2 are the amino acid sequence of modified GFP variants. Sequence Id. Nos. 3 and 4 are the amino acid sequence of modified YFP variants. Sequence Id. Nos. 5 and 6 are the amino acid sequence of modified CFP variants. Sequence Id. Nos. 7 and 8 show the amino acid sequence of modified BFP variants. The digested elements of these proteins had fluorescent properties that can be used for a novel sensor of this invention.

In many examples, the fluorescent sensor had between about 155 to about 190 amino acids. In one example, the fluorescent sensor was found to have 181 amino acids and to be 20373.79 Daltons in mass. In another example, the fluorescent sensor was found to have 184 amino acids and to be of 2864.68 Daltons in mass. Another illustrative fluorescent sensor can have about 157 amino acids. As such, the fluorescent sensors are not naturally occurring.

Sequence Id. Nos. 9 through 12 and Sequence Id. Nos. 13 through 16 are amino acid sequences of exemplary fluorescent sensors. As may be seen from the amino acid sequences, the fluorescent sensors comprise the chromophore sequence threonine-tyrosine-glycine (T-Y-G). This chromophore sequence is responsible for the fluorescent sensor's unexcited emission in the yellow-green band of the radiation spectrum and the excited emission maximum at 503 nm, which is distinct from eGFP and modified eGFP. Many of the fluorescent sensors appear to have an emission pattern similar to unmodified eGFP in the band between about 400 and 500 nm.

Sequence Id. Nos. 17 through 19 show amino acid sequences of exemplary complimentary fragments obtained from the digestions of various modified proteins. For example, Sequence Id. Nos. 18 is the complimentary fragment generated from trypsin cleavages. The amino acid sequences generated by the trypsin cleavages can form an enhanced fluorescence complex with the fluorescent proteins encoded by Sequence Id. Nos. 13 through 16.

Figure 3:
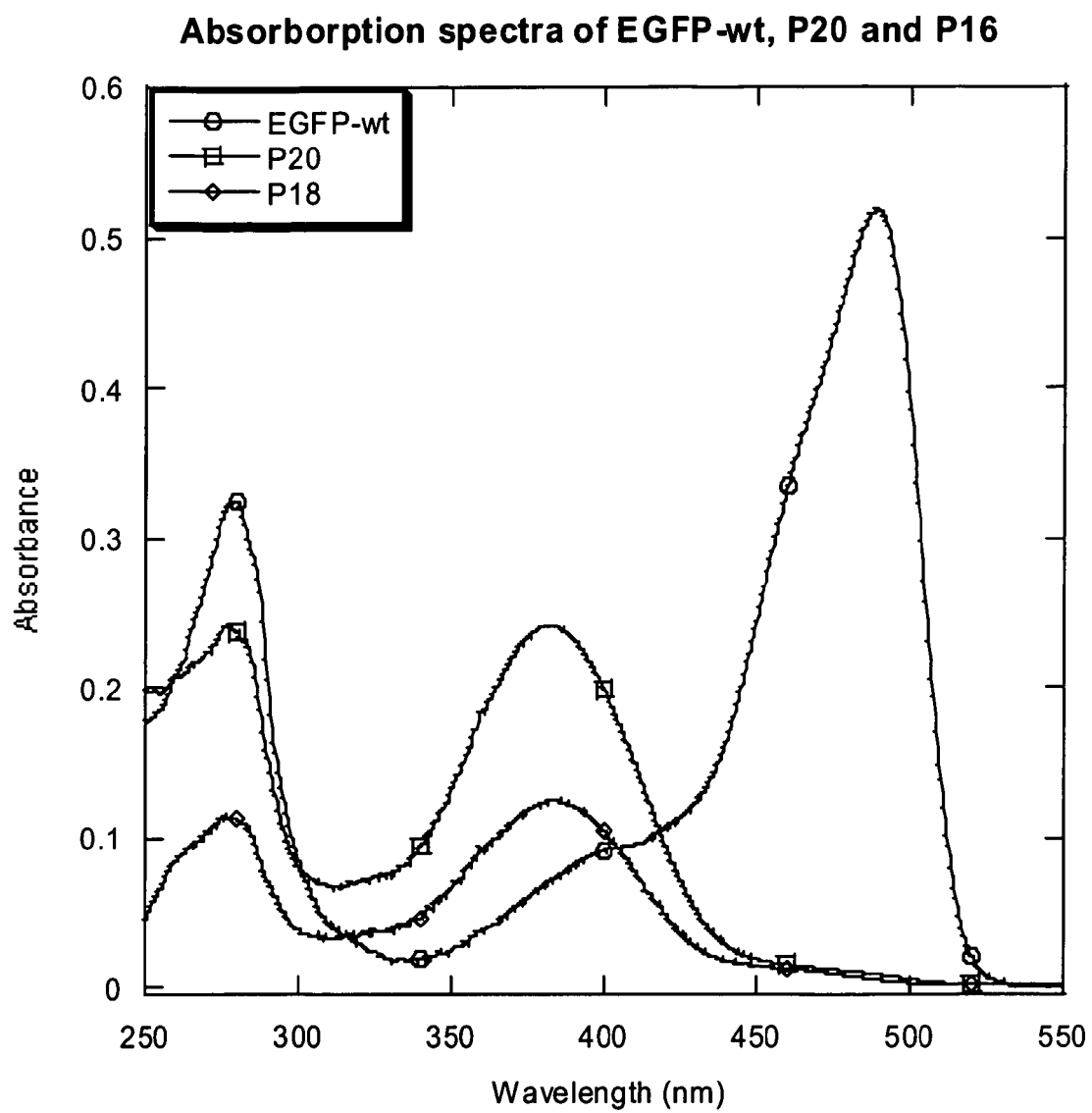
FIG. 3 represents the UV absorbance spectra of w.t. EGFP and further examples of the P20 sensor.

FIG. 3 shows that the UV absorbance spectra of various fluorescent sensors have a strong absorbance at 383 nm. As shown in FIG. 3, a comparison of the emission spectra from the modified eGFP prior to trypsin digestion and from the fluorescent sensor shows that the fluorescent sensor has a more intense emission band at 383 nm. The fluorescent sensor continues to have an emission pattern comparable to that of the unmodified eGFP and the modified eGFP. The fragment identified as P16 is a slightly smaller fragment. While emission of the fluorescent sensors may be measurable and detectable, the fluorescence intensity may be about 50 fold weaker than the intact protein of either the modified eGFP or the unmodified eGFP.

Figure 6:
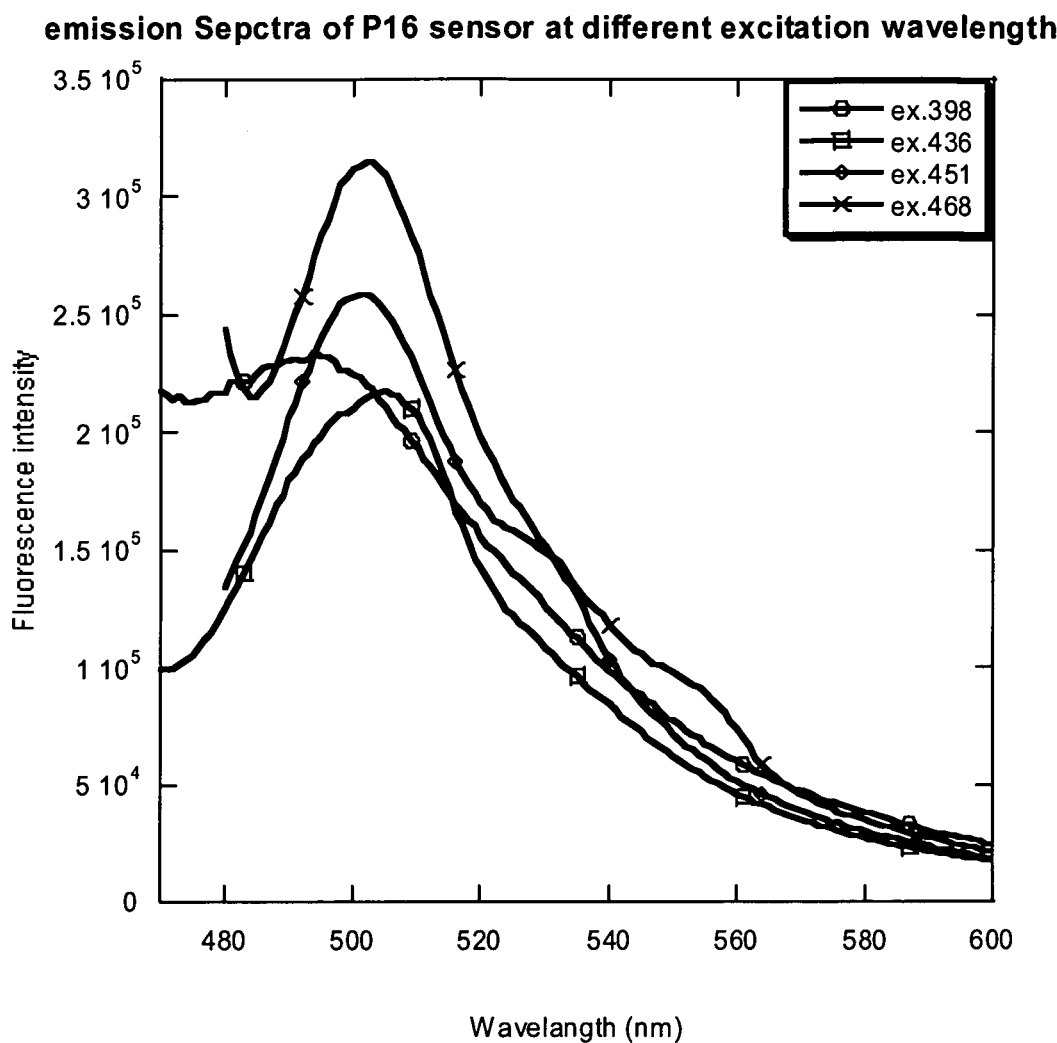
FIG. 6 shows the excitation and emission spectra of another example of the miniature sensor.

FIG. 4 through FIG. 5 and FIG. 6 show the excitation and emission spectra of two examples of the fluorescent sensor, which in these examples were in the green band. The fluorescent sensors have an emission maximum of about 503 nm, when excited at radiation at 398, 469 and 483 nm. As shown in FIG. 4, the larger sensor emits a stronger emission peak at about 503 nm when exited with radiation at wavelengths of 383 nm (FIG. 4), 398 nm (FIG. 5), 469 nm (not shown), and 483 nm (not shown). Similarly as shown in FIG. 6, a smaller fragment showed an emission at 503 nm when excited with radiation at wavelengths of 383 nm, 398 nm, 469 nm, and 483 nm. The brightness and/or emission was found to have a quantum yield of about 0.04, which can be detectable by optical equipment.

Figure 7:
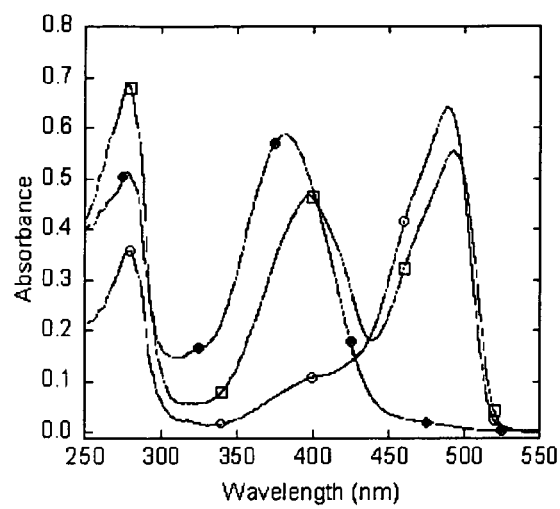
FIG. 7 shows the excitation spectrum of the fluorescent sensor whose maximum was found to between 469 and 483 nm.
Figure 8:
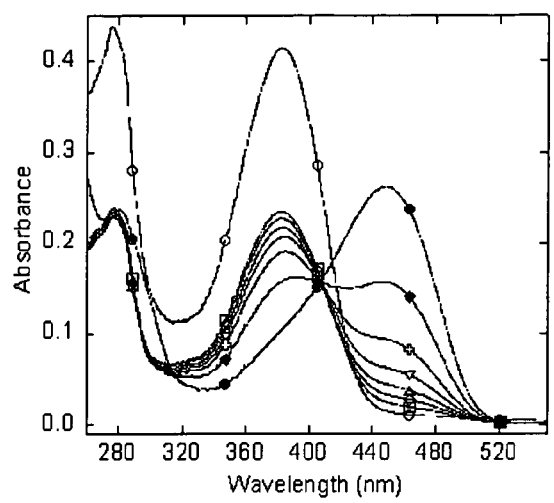
FIG. 8 shows the fluorescence maximum emission was found to be at 483 nm.

FIG. 7 and FIG. 8 show the excitation scans of a fluorescent sensor. FIG. 7 shows the excitation spectrum of the fluorescent sensor whose maximum was found to between 469 and 483 nm. FIG. 8 shows the fluorescence maximum emission was found to be at 483 nm, but showed significant fluorescence emissions at various wavelengths. Excitation wavelength at 398 nm (○), at 469 nm (□) and at 483 nm (◇) is shown in FIG. 8.

Figure 9:
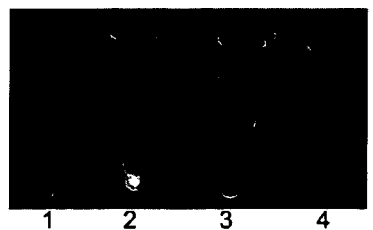
FIG. 9 shows the course of digestions of a modified GFP suitable for use with the present invention and that can be digested with trypsin into the miniature sensor and the complementary fragment.
Figure 10:
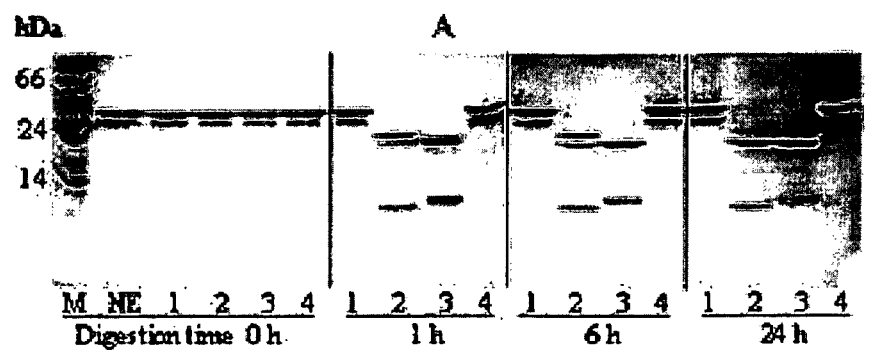
FIG. 10 shows evidence that the digestion can result in a miniature sensor.
Figure 11:
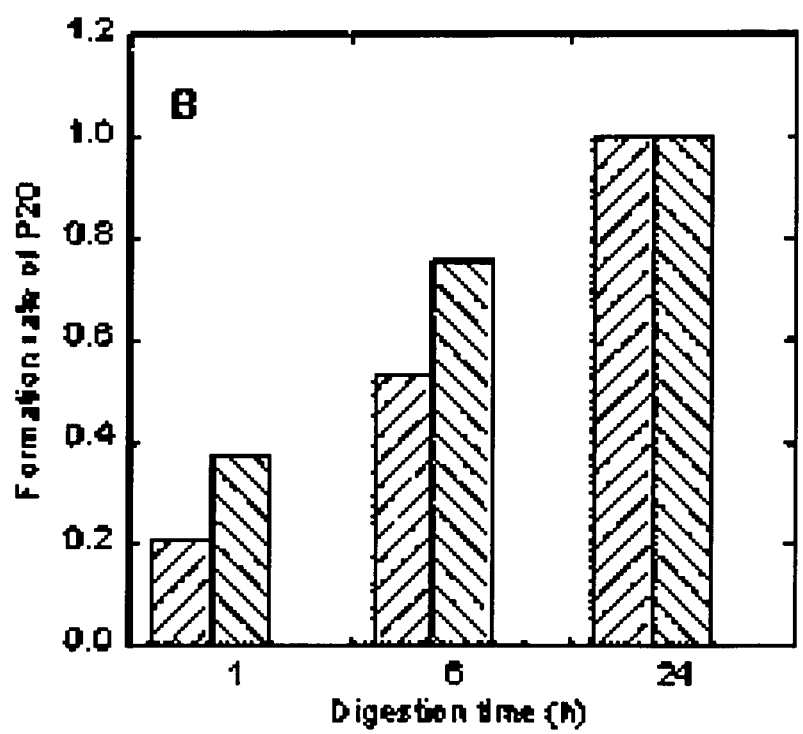
FIG. 11 shows fluorescent sensor acting as a pH indicator.

FIG. 9, FIG. 10, and FIG. 11 show that the emission of a fluorescent sensor can dependant on the pH of the environment. As can be seen, the absorbance maximums can depend on the pH of the sample environment (pH 3.32 (○), fragment P20 at pH 7.32 (□) and fragment fluorescent at pH 10.82 (●)). For example, at a pH of 10.8, the peak absorbance was at about 450 nm. In fact, the absorption spectra of fluorescent (the maximum absorption at 383 nm decreases and the maximum absorption at 454 nm increases as the increase of pH values from about 3 to about 11. In one example, the fluorescent sensor was able to detect pH values between about 3.3 to about 10.8. There is quantifiable relationship between peak absorbance and the pH of the sample, which allows the optical properties of the fluorescent sensor to detect pH changes in a sample.

The fluorescent sensor can be used a probe to identify protein-protein or protein-peptide interactions both in vitro and in vivo. The assembling of a fluorescent sensor with other proteins or peptides may dramatically increase the fluorescence or absorbance signal. Specifically, these interactions may be screened based on the assembly of the fluorescent sensor fused to a first protein and a smaller fragment fused to the interacting protein which is schematically shown in FIG. 1. Such interactions may be monitored by measuring the fluorescence or the change of fluorescence from the fluorescent sensor. In addition, both protein fragments expressed in bacteria, mammalian and in vitro systems can be used directly to monitor the interactions with fused partners in cell lysates, at the extracellular spaces, or tissue samples. They can be very useful for high throughput screening of drug discovery and identification for new target validations of diseases.

Other Uses of Fluorescent Protein Variants

The fluorescent sensor can be useful in any method that employs a fluorescent protein. The fluorescent sensor can be useful as fluorescent markers in the many ways fluorescent markers already are used, including, for example, coupling fluorescent protein variants to antibodies, polynucleotides or other receptors for use in detection assays such as immunoassays or hybridization assays, or to track the movement of proteins in cells. For intracellular tracking studies, a first (or other) polynucleotide encoding the fluorescent protein variant is fused to a second (or other) polynucleotide encoding a protein of interest and the construct, if desired, can be inserted into an expression vector. Upon expression inside the cell, the protein of interest can be localized based on fluorescence, without concern that localization of the protein is an artifact caused by oligomerization of the fluorescent protein component of the fusion protein.

Further, the fluorescent sensor can be useful in systems to detect induction of transcription. For example, a nucleotide sequence encoding a non-fluorescent protein can be fused to a promoter or other expression control sequence of interest, which can be contained in an expression vector, the construct can be transfected into a cell, and induction of the promoter (or other regulatory element) can be measured by detecting the presence or amount of fluorescence, thereby allowing a means to observe the responsiveness of a signaling pathway from receptor to promoter.

Further, the present invention provides a method for identifying the presence of a molecule in a sample. Such a method can be performed, for example, by linking a fluorescent protein variant of the invention to the molecule, and detecting fluorescence due to the fluorescent protein variant in a sample suspected of containing the molecule. The molecule to be detected can be a polypeptide, a polynucleotide, or any other molecule, including, for example, an antibody, an enzyme, or a receptor, and the fluorescent protein variant can be a tandem dimer fluorescent protein.

A method of identifying an agent or condition that regulates the activity of an expression control sequence also is provided. Such a method can be performed, for example, by exposing a recombinant nucleic acid molecule, which includes a polynucleotide encoding a fluorescent protein variant operatively linked to an expression control sequence, to an agent or condition suspected of being able to regulate expression of a polynucleotide from the expression control sequence, and detecting fluorescence of the fluorescent protein variant due to such exposure. Such a method is useful, for example, for identifying chemical or biological agents, including cellular proteins, that can regulate expression from the expression control sequence, including cellular factors involved in the tissue specific expression from the regulatory element. As such, the expression control sequence can be a transcription regulatory element such as a promoter, enhancer, silencer, intron splicing recognition site, polyadenylation site, or the like; or a translation regulatory element such as a ribosome binding site.

The present invention also provides a method for determining whether a sample contains an enzyme. Such a method can be performed, for example, by contacting a sample with a second fluorescent protein variant of the invention; wherein the presence of an enzyme in the sample results in a change in the degree of fluorescence resonance energy transfer. Similarly, the present invention relates to a method for determining the activity of an enzyme in a cell. Such a method can be performed, for example, providing a cell that expresses a fluorescent protein variant construct, wherein the peptide linker moiety comprises a cleavage recognition amino acid sequence specific for the enzyme coupling the donor and the acceptor; exciting said donor, and determining the degree of fluorescence resonance energy transfer in the cell, wherein the presence of enzyme activity in the cell results in a change in the degree of fluorescence resonance energy transfer.

Also provided is a method for determining the pH of a sample. (see FIGS. 9, 10, and 11). Such a method can be performed, for example, by contacting the sample with a first fluorescent protein variant, which can be a fluorescent protein, wherein the emission intensity of the first fluorescent protein variant changes as pH varies between pH 5 and pH 10; exciting the indicator; and determining the intensity of light emitted by the first fluorescent protein variant at a first wavelength, wherein the emission intensity of the first fluorescent protein variant indicates the pH of the sample. The first fluorescent protein variant useful in this method, or in any method of the invention, can comprise Sequence Id No. 2 or 3. It will be recognized that such fluorescent protein variants similarly are useful, either alone or in combination, for the variously disclosed methods of the invention.

Kits.

A kit for use in transfecting host cells may be assembled using the nucleic acid molecules encoding the fluorescent sensors, or for labeling target polypeptides with the fluorescent sensor. Host cell transfection kits may comprise at least one container containing one or more of the nucleic acid molecules encoding a fluorescent sensor (or a composition comprising one or more of the nucleic acid molecules or plasmids described above), which nucleic acid molecule preferably comprises plasmid. These transfection kits of this invention optionally further may comprise at least one additional container that may contain, for example, a reagent for delivering the fluorescent sensor nucleic acid molecule into a host cell.

Further, kits can contain chemical reagents (e.g., polypeptides or polynucleotides) as well as other components. For example, kits can also include, for example but not limited to, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, instructions to the kit user, solutions, buffers or other chemical reagents, suitable samples to be used for standardization, normalization, and/or control samples. Kits of the present invention can also be packaged for convenient storage and safe shipping, for example, in a box having a lid. In some embodiments, for example, kits of the present invention can provide a fluorescent protein of the invention, a polynucleotide vector (e.g., a plasmid) encoding a fluorescent protein of the invention, bacterial cell strains suitable for propagating the vector, and reagents for purification of expressed fusion proteins.

Polypeptide labeling kits according to the present invention may comprise at least one container containing, for example, a fluorescent sensor such as those described above (or a composition of the invention comprising a chromophore from a GFP), which is preferably a fluorescent having an amino acid sequence as set forth in Sequence Id. Nos. 9-16 and/or the nucleic acid sequence corresponding thereto. These labeling kits of this invention further may comprise at least one additional container which may contain, for example, a reagent for covalently linking the fluorescent sensor to the target polypeptide. It is understood that proteins can be deposited directly into cells as means of delivering the fluorescent protein to the sample.

In one embodiment, the fluorescent sensor may be linked to an analyte binding peptide so to create an analyte fluorescent sensor. This fluorescent sensor may be used to detect and quantify the analyte concentration and flux thereof in a sample as a non-ratiometric dye. More particularly, the analyte fluorescent sensor is inserted into the sample, the sample then is excited by radiation, the fluorescence from the sample then is measured using an optical device, and the fluorescence or flux thereof then is analyzed to quantify or detect the analyte concentration in the sample. In order to analyze the sample, it may be necessary to generate a standard curve based on the fluorescence generated from known analyte concentrations. Specifically, the fluorescence signal of the analyte sensor is compared to the fluorescence of the standard curve so as to determine the concentration of analyte in the sample.

Fluorescent sensors and kits using such proteins may be used in a variety of applications. For example, the fluorescent sensors are useful as reporter genes that allow a determination of transfection efficiency and success. Alternatively, the fluorescent sensors themselves may be used as fluorescent labels suitable for detectably labeling other proteins, nucleic acids or particulates to be used in a variety of applications, such as labeling antibodies used in infectious disease diagnostic methods. The fluorescent sensors may be attached to target polypeptides and proteins by a variety of methods that are well-known to one of ordinary skill in the art, including the use of chemical coupling reagents. Importantly, use of the fluorescent sensors that emit fluorescence when illuminated by white light will spare the user the considerable expense and technical difficulty that can accompany the use of fluorescent optics for the examination of fluorescent reporter genes such as fluorescent sensors.

Samples Useful with this Invention

The samples useful with this include biological samples, environmental samples, or any other samples for which it is desired to determine whether a particular molecule is present therein. With some embodiments, the sample can include a cell or a cell extract, which may be been obtained from an animal (e.g, mammal or humans) or a plant. Alternatively, the cells can originate from or be derived from bacterial cells.

Further, the cells may be obtained from a culture of such cells, for example, a cell line, or can be isolated from an organism. As such, the cell can be contained in a tissue sample, which can be obtained from an organism by any means commonly used to obtain a tissue sample, for example, by biopsy of a human. Where the method is performed using an intact living cell or a freshly isolated tissue or organ sample, the presence of a molecule of interest in living cells can be identified, thus providing a means to determine, for example, the intracellular compartmentalization of the molecule.

One of ordinary skill in the art may select a suitable sample without undue experimentation.

Measuring Fluorescence

Methods for detecting the fluorescent sensor or of a cell expressing a fluorescent sensor may comprise, for example, illuminating the fluorescent sensor or cell expressing the fluorescent sensor with an illumination source such that the fluorescent sensor or cell expressing the fluorescent sensor emits radiation. Such detection methods may use an illumination source such as an incandescent light source, a fluorescent light source, a halogen light source, sunlight, and other equivalent sources. When illuminated by such an illumination source, the fluorescent sensor will emit fluorescent light that may be detected by unaided observation or by other qualitative or quantitative methods. Suitable methods for measuring fluorescence of samples are known and understood by those with ordinary skill in the art.

Alternatively, the fluorescence signal and absorbance may be measured directly from the fluorescent sensor. As the fluorescent sensor has a strong absorbance at 398 nm, the absorption at 398 nm may be used to detect the fluorescent sensor. Further, the fluorescent sensor may be detected directly from a fluorescence emission at 503 nm.

Suitable methods for measuring fluorescence of samples are known and understood by those with ordinary skill in the art. Preferred methods for measuring fluorescence should be capable of measuring the fluorescence of the ion species and determining the ion concentration. Some representative known methods of performing assays on fluorescent materials are described in, e.g., Lakowicz, J. R., Principles of Fluorescence Spectroscopy, (Plenum Press 1983); Herman, B., Resonance Energy Transfer Microscopy, Fluorescence Microscopy of Living Cells in Culture, Part B, Methods in Cell Biology, vol. 30, pp. 219-243 (ed. Taylor, D. L. & Wang, Y.-L., Academic Press 1989); Turro, N.J., Modern Molecular Photochemistry, pp. 296-361 (Benjamin/Cummings Publishing, Inc. 1978). Further, there are numerous commercial apparatuses and set-ups for determining and measuring the fluorescence of a sample, which include fluorescence spectroscopy, fluorescence microscopy, and confocal laser scanning microscopy. Such methods are readily available or easily researchable in available publications.

One method for measuring fluorescence in samples is through the use of fluorimeters. Radiation is passed through the sample under controlled conditions (e.g. constant temperature and pressure). As the radiation passes through the sample at an excitation wavelength, the fluorescence sensor in the sample emits distinct spectral properties (such as emission spectra), which then are captured as data by the optics of the fluorimeter. Both excitation and emission spectra are taken to determine the excitation and emission maxima for optimal fluorescence signals and parameters, which depend on the microenvironments. Optimal fluorescence signal may be obtained at any excitation and emission wavelengths near respective corresponding maxima. The data is saved on a computer and or it can be further analyzed by computer. The scanned data then is compared to control samples, i.e. calibration samples, so to determine the concentration of the analyte in the sample. Specifically, the analyte concentration may be determined by extrapolating the fluorescence of the sample with a calibration curve. This assay may be applied to purified fluorescent proteins or any cell mixture with expressed fluorescent proteins Production and Expression of the Fluorescent Sensor Based on the fluorescence properties of the fluorescent sensor, a DNA construct of the sensors may be inserted into a recombinant vector or any suitable vector that may conveniently be subjected to recombinant DNA procedures. The specific vector can depend on the type of host cell. For example, recombinant DNA plasmid vectors, which can exist as an extrachromosomal entity, may be a suitable vector. Alternatively, the vector may be one that, when introduced into a host cell, is integrated into the host cell genome and replicated together with the chromosome(s) into which it has been integrated. Once the fluorescent sensor has been constructed, vectors comprising the fluorescent nucleic acid molecules may be formulated into a variety of compositions, such as solutions (for example, buffer solutions) to be used in transfecting host cells.

A fluorescent protein variant can be linked to the molecule directly or indirectly, using any linkage that is stable under the conditions to which the protein-molecule complex is to be exposed. Thus, the fluorescent protein and molecule can be linked via a chemical reaction between reactive groups present on the protein and molecule, or the linkage can be mediated by linker moiety, which contains reactive groups specific for the fluorescent protein and the molecule. It will be recognized that the appropriate conditions for linking the fluorescent protein variant and the molecule are selected depending, for example, on the chemical nature of the molecule and the type of linkage desired. Where the molecule of interest is a polypeptide, a convenient means for linking a fluorescent protein variant and the molecule is by expressing them as a fusion protein from a recombinant nucleic acid molecule, which comprises a polynucleotide encoding, for example, a fluorescent protein operatively linked to a polynucleotide encoding the polypeptide molecule.

Expression of the Fluorescent Sensor

The fluorescent sensor may be produced as chimeric proteins by recombinant DNA technology. Recombinant production of proteins including fluorescent proteins involves expressing nucleic acids having sequences that encode the proteins. Nucleic acids encoding fluorescent proteins can be obtained by methods known in the art. For example, a nucleic acid encoding the protein can be isolated by a polymerase chain reaction of DNA from *A. victoria* using primers based on the DNA sequence of *A. victoria* GFP. Mutant versions of fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

In the chimeric proteins of the invention, the sensor polypeptide is inserted into an optically active polypeptide, which responds (e.g., a conformation change) to, for example, a cell signaling event. Cell signaling events that occur in vivo can be of a very short duration. The optically active polypeptides of the invention allow measurement of the optical parameter, such as fluorescence, which is altered in response to the cell signal, over the same time period that the event actually occurs. Alternatively, the response can be measured after the event occurs (over a longer time period) as the response that occurs in an optically active polypeptide can be of a longer duration than the cell signaling event itself.

In the present invention, the nucleic acid sequences encoding the fluorescent sensor may be inserted into a recombinant vector, which may be plasmids, viruses or any other vehicle known in the art, that has been manipulated by the insertion or incorporation of the nucleic acid sequences encoding the chimeric peptides of the invention. The recombinant vector typically contains an origin of replication, a promoter, as well as specific genes that allow phenotypic selection of the transformed cells. Vectors suitable for use in the present invention include but are not limited to the T7-based expression vector for expression in bacteria or viral vectors for expression in mammalian cells, baculovirus-derived vectors for expression in insect cells, and cauliflower mosaic virus (CaMV), tobacco mosaic virus (TMV), and other vectors.

Depending on the vector utilized, any of a number of suitable transcription and translation elements, including constitutive and inducible promoters, transcription enhancer elements, transcription terminators, etc., may be used in the expression vector. Such construction of expression vectors and the expression of genes in transfected cells can involve the use of molecular cloning techniques (e.g. in vitro recombinant DNA techniques, synthetic techniques and in vivo recombination/genetic recombination), bacterial system for the expression of vectors, yeast systems with constitutive or inducible promoters, insect systems, prokaryotic and eukaryotic systems using transfection or co-transfections of DNA vectors, transgenic animals using for example viral infection, and embryonic stem cells. Methods and procedures for using and applying such vectors are widespread in publications and are known or easily obtainable by persons of ordinary skill in the art.

Further, the fluorescent sensor may be produced as chimeric proteins by recombinant DNA technology. Recombinant production of proteins including fluorescent proteins involves expressing nucleic acids having sequences that encode the proteins. Nucleic acids encoding fluorescent proteins can be obtained by methods known in the art. For example, a nucleic acid encoding the protein can be isolated by a polymerase chain reaction of DNA from A. victoria using primers based on the DNA sequence of A. victoria GFP. Mutant versions of fluorescent proteins can be made by site-specific mutagenesis of other nucleic acids encoding fluorescent proteins, or by random mutagenesis caused by increasing the error rate of PCR of the original polynucleotide with 0.1 mM $MnCl_2$ and unbalanced nucleotide concentrations.

In terms of expression, the nucleic acid sequences encoding the fluorescent sensor may be inserted into a recombinant vector, which may be plasmids, viruses or any other vehicle known in the art, that has been manipulated by the insertion or incorporation of the nucleic acid sequences encoding the chimeric peptides of the invention. The recombinant vector typically contains an origin of replication, a promoter, as well as specific genes that allow phenotypic selection of the transformed cells. Vectors suitable for use in the present invention include but are not limited to the T7-based expression vector for expression in bacteria or viral vectors for expression in mammalian cells, baculovirus-derived vectors for expression in insect cells, and cauliflower mosaic virus (CaMV), tobacco mosaic virus (TMV), and other vectors.

In one embodiment, the fluorescent sensor-containing plasmid vectors are transformed into a competent host cell, which may be a bacterium, yeast, insect cell, or mammalian cell. Transformation of host cells may be accomplished by any technique generally used for introduction of exogenous DNA, including the chemical, viral, electroporation, lipofection and microinjection methods that are well-known in the art. After expansion of transformed cultures, mutated GFP cDNA is isolated from the host cells by routine methods and is subcloned into a plasmid backbone for use in subsequent transfections.

Depending on the vector utilized, any of a number of suitable transcription and translation elements, including constitutive and inducible promoters, transcription enhancer elements, transcription terminators, etc., may be used in the expression vector. Such construction of expression vectors and the expression of genes in transfected cells can involve the use of molecular cloning techniques (e.g. in vitro recombinant DNA techniques, synthetic techniques and in vivo recombination/genetic recombination), bacterial system for the expression of vectors, yeast systems with constitutive or inducible promoters, insect systems, prokaryotic and eukaryotic systems using transfection or co-tranfections of DNA vectors, transgenic animals using for example viral infection, and embryonal stem cells. Methods and procedures for using and applying such vectors are widespread in publications and are known or easily obtainable by persons of ordinary skill in the art.

Targeting the Fluorescent Sensor

The fluorescent sensor may include a nucleotide targeting sequence that directs the fluorescent protein to particular cellular sites. By fusing the appropriate organelle targeting signal proteins or localized host proteins to the fluorescent proteins, the fluorescent protein may be selectively localized in cells. Such a targeting sequence, which may code for organelle targeting signal or host proteins, may be ligated to the 5' terminus of a nucleotide, thus encoding the fluorescent protein such that the targeting peptide is located at the amino terminal end of the fluorescent protein.

Such signal proteins are known to those with ordinary skill in the art and may be readily obtained without undue experimentation or research. For example, the fluorescent protein may be directed to and transported across the endoplasmic reticulum by fusing the appropriate signal protein. Once secreted, the protein then is transported through the Golgi apparatus, into secretory vesicles, and into the extracellular space, preferably, the external environment. Signal peptides or proteins that may be used with this invention include pre-pro peptides that contain a proteolytic enzyme recognition site.

The localization sequence may be a nuclear localization sequence, an endoplasmic reticulum localization sequence, a peroxisome localization sequence, a mitochondrial localization sequence, or a localized protein. Localization sequences may be targeting sequences that are described, for example, in Stryer, L., Biochemistry, Chapter 35—Protein Targeting (4th ed., W. H. Freeman, 1995). Some known localization sequences include those targeting the nucleus (KKKRK) (SEQ ID NO. 21), mitochondrion (amino terminal MLRTSSLFTRRVQPSLFRNILRLQST-) (SEQ ID NO. 22), endoplasmic reticulum (KDEL) at C-terminus, assuming a signal sequence present at N-terminus, e.g. MLLSVPLLGLLG-LAAD) (SEQ ID NO. 23), peroxisome (SKF at the C-terminus), synapses (S/TDV or fusion to GAP 43, kinesin and tau), prenylation or insertion into plasma membrane (CAAX, CC, CXC, or CCXX at C-terminus), cytoplasmic side of plasma membrane (chimeric to SNAP-25), or the Golgi apparatus (chimeric to furin). One of ordinary skill in the art can determine localization sequences suitable to the present invention without undue research and experimentation.

Method for Preparing Fluorescent Sensors

While the fluorescent sensors may be prepared using the nucleic acids or the amino acid sequences disclosed herein together with ordinary skill the art, fluorescents sensors also can be prepare through enzymatic digestion. In this embodiment, the fluorescent sensor is prepared using the steps of (a) providing a protein with a cleavage site or introducing a cleavage site into the protein; and (b) digesting the protein with an enzyme suitable for the cleave site.

The "protein" suitable with this method can be any protein that can fluoresce when excited with an appropriate electromagnetic radiation that derives its fluorescence from autocatalytically forming a chromophore. A fluorescent protein can contain amino acid sequences that are naturally occurring or that have been engineered.

3. Examples

Plasmid Construction

A nucleotide sequence encoding the fluorescent sensor (Sequence Id. Nos. 9 through 17) and/or the complementary segment (Sequence Id. Nos. 8 and 9) was inserted in to a Pet28a plasmid using polymerase chain reaction (PCR) technique. The sequence of constructed plasmid was verified through automated DNA sequence analysis.

Protein Expression

A protein encoding the fluorescent sensor was expressed in a single colony that was inoculated with 20 ml of LB media with 30 μg/ml kanamycin at 37 C and agitated at 200 rpm overnight and then transferred to 1 L of LB media. The cell culture was induced with 0.2 mM isopropyl-p-D-thiogalactopyranoside (IPTG) after the $O.D._{600nm}$ reached 0.6 and allowed to grow at 30 C for another 16 to 20 h.

After the proteins were then purified, the cell pellets were resuspended in a lysis buffer and sonicated to disrupt the cell membrane. The resulting solution was centrifuged at 20000 g for 20 min, and the supernatant was filtered and injected into a nickel-chelating column on fast performance liquid chromatography (FPLC). After washing the supernatant with a buffer, the bound protein was eluted with a gradient of imidazole from 0 to 0.5 M in phosphate buffer and the purity of the fractions was monitored by SDS-PAGE.

The protein collected from FPLC was dialyzed into 10 mM Tris buffer with 1 mM DTT at pH 7.4 to remove imidazole. The concentration of purified protein was determined by UV-visible absorbance at 280 nm with an extinction coefficient of 21,890 $M^{-1}$ $cm^{-1}$.

Stability of an Exemplary Fluorescent Protein ("P20 Sensor")

After natural degradation or protease digestion of exemplary protein (modified EGFP) encoded by Sequence ID. Nos. 1 through 8, the mixture of products showed a strong green fluorescence. In order to investigate the source of the fluorescence, fast performance liquid chromatography (FPLC) and high-pressure liquid chromatography (HPLC) were utilized to separate protein fragments in denatured conditions. Urea was added to digested products and the solution was heated for 5 min to denature the protein fragments. The denatured protein fragments were injected to into a prepared FPLC connected a Hitrap Sephadex 75 size exclusion column and eluted with 10 mM Tris buffer containing 6 M urea at pH 7.4. The major fragments were collected and further purified by reversed-phase HPLC equipped with a Whatman $C_4$ column through gradient elution of mobile phase A ($H_2O$ containing 0.1% TFA) and mobile phase B (100% acetonitrile containing 0.1% TFA). The fractions with purified protein fragments were lyophilized in a speed vacuum for analyses of protein sequence and spectral properties.

Figure 12:
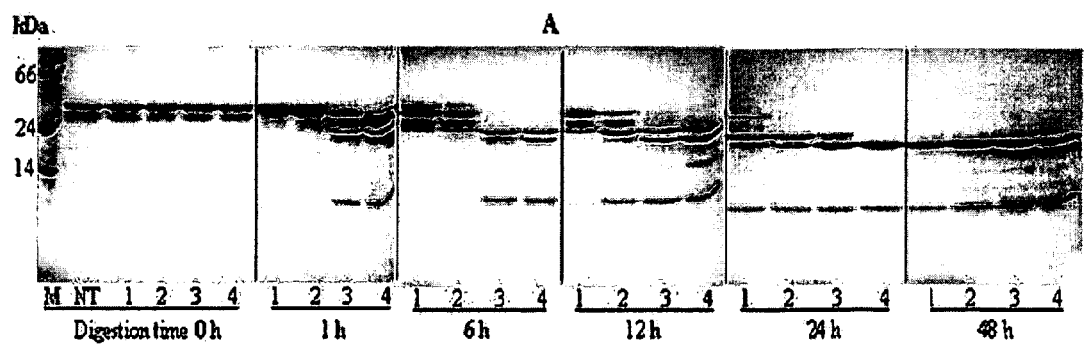
FIG. 12 shows the course of digestions of another modified GFP suitable for use with the present invention and that can be digested with trypsin into the miniature sensor and the complementary fragment.
Figure 13:
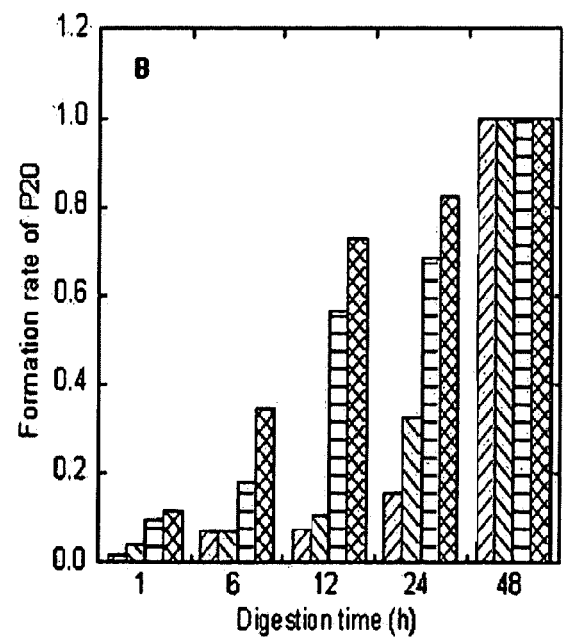
FIG. 13 shows evidence that the digestion can result in a miniature sensor.
Figure 14:
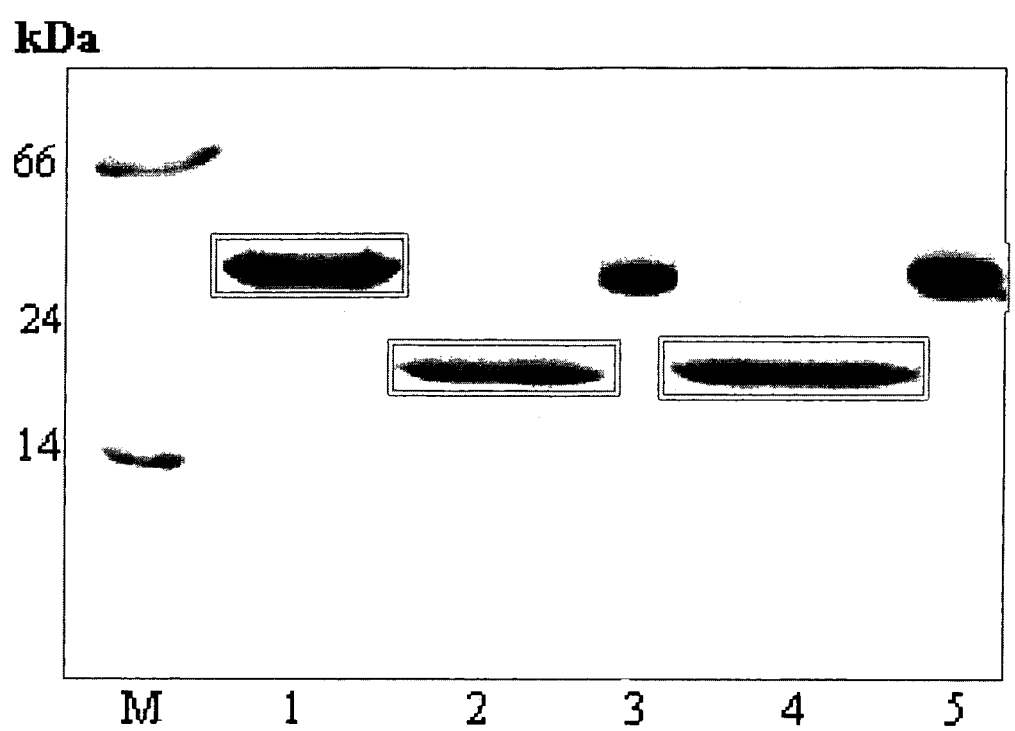
FIG. 14 shows gel electrophoresis studies showing bands corresponding to the digested fragments of a modified GFP.

FIGS. 12 and 13 shows the formation of an exemplary protein ("P20") based on the optical density of its band in SDS-PAGE after cleavage by Trypsin at various time intervals FIG. 14 shows SDS-PAGE (A) of modified EGFP digested with different concentrations of trypsin for 0, 1, 6, 12, 24, and 48 h at room temperature. Unlike w.t. EGFP remains uncleaved after incubation with these proteinases for over a week, the modified EGFP proteins were cleaved by trypsin and chymotrypsin within 1 h. The intact protein (34 kDa) was first cleaved by trypsin into three fragments with molecular weights of 23, 20 and 8 kDa after digestion for 1 to 6 h.

The fragment of 23 kDa is further digested and converted to 20 kDa fragment at a digestion time of 24 h, while the 8 kDa band remained unchanged. Similarly, chymotrypsin cleaved the protein into three fragments of 21, 20 and 10 kDa, respectively. The 21 kDa band was reduced to a 20 kDa when the digestion time was 6 h or longer. Finally, modified EGFP was cleaved by chymotrypsin and trypsin into two stable fragments. The large fragments have similar molecular weights (approximately 20 kDa, P20) while the small fragments have molecular weight of 8 kDa (P8) or 10 kDa (P10). The P8 and P10 fragments remained unchanged after more than 24 h of digestion. In summary, modified EGFP was specifically cleaved by trypsin and chymotrypsin at preferable sites and the cleavage process stopped after the preferable sites were completely cleaved. Moreover, after modified EGFP was completely cleaved into two major fragments by trypsin and chymotrypsin, the cleaved protein solution still retained its original green fluorescent color.

Optical Characterization of an Exemplary Fluorescent Protein ("P20")

To examine the optical properties of digested fragments, the purified fractions of P20 and P8 collected were lyophilized. P20 exhibits yellowish green color while P8 is colorless. The green fluorescence of P20 was observed under UV light. When P20 was dissolved in water or 10 mM Tris buffer, it emitted a weak green fluorescence under UV light, as shown in FIG. 4 (top). This result indicates that P20 contains a mature chromophore in water or 10 mM Tris buffer without the help of P8.

The UV-visible spectrum shows that P20 has a strong absorbance peak at 383 nm. Compared with intact modified EGFP, the absorbance peak of P20 is blue shifted from 397 to 383 nm. This absorption wavelength is same as that of EGFP-wt in acid denatured condition (pH 3.36). After trypsin digestion, the presence of only one absorption peak of P20 at 383 nm is possibly due to the removal of Ser203 and Glu222 for presenting the neutral chromophore. In addition, the absorbance intensity at 383 nm decreases and the absorbance intensity at 454 nm increases as the increase of pH (FIG. 4). The isosebatic point of absorbance at 410 nm also indicates the chromophore still has two convertible states at various pH conditions. P20 has two excitation peaks at 469 and 483 nm, and an emission peak at 503. This excitation wavelength is similar to the EGFP-wt and the emission peak has a slight blue shift.

As shown in FIG. 3, the maximum emission of 503 nm is independent of the excitation wavelength (398, 469, or 483 nm). Meanwhile, the fluorescence intensity of P20 is only approximately 1/50 of intact modified EGFP variant. An observed decrease in fluorescence of P20 is possibly due to disruption of the compact structure and incomplete refolding. Compared with current reported research results that the minimum domain for fluorescence of GFP is amino acid from 7 to 229, this mini-GFP with weak green fluorescence is smaller and is greatly decreased in the number of amino acids for fluorescence in GFP. However, the chromophore refolding mechanism in this mini-GFP and the structural difference between mini-GFP and other EGFP variants are still unknown.

The optical properties of P20 were monitored by a UV-1601 spectrophotometer and a fluorescence spectrophotometer. The UV-visible spectra of the fragments was scanned from 600 nm to 200 nm in 10 mM Tris, 1 mM DTT, pH 7.4.

The UV-visible spectra at different pH conditions were monitored by adding NaOH in a gradient. The final pH value was 10.82 after addition of NaOH.

The optical properties were also monitored by UV-visible spectrophotometer and a fluorescence spectrophotometer. The UV-visible spectra at various pH conditions were scanned for investigating the optical property of P20 as function of pH. The fluorescence spectra of exemplary P20 were measured in the emission region of 410 nm to 600 nm with an excitation wavelength at 398 nm and in emission region of 500 nm to 600 nm with an excitation wavelength at 469 and 483 nm, respectively. It was found the optical properties changed with the pH of the sample.

EGFP variants with cleavage sequence grafted at 157 and 172 are fluorescent in bacteria and as purified proteins suggesting the formation of chromophore.

Fluorescent Sensor Complexes

The digested two major fragments with molecular mass of 20 kDa and 8 kDa or 20 kDa and 10 kDa were co-eluted out and shown in SDS-PAGE while using Sephadex 75 size exclusion column or Hitrap Q column with salt gradient elution. The pure P20 fragment was first obtained using SDS-PAGE by excising the corresponding band and eluting the protein out in a Tubeluta tube with dialysis membrane. Because the amount of P20 fragment was limited from SDS-PAGE electroelution and because P8 fragment was difficult to purify, purification by combinative FPLC and HPLC under the condition of 6 M urea for denaturation was performed. Similar results were obtained in the N-terminal sequence analysis and molecular weight analysis of P20 and P8 fragments that were separated with either SDS-PAGE electroelution or combinative FPLC or HPLC.

As has been discussed above, there were always two bands in SDS-PAGE after cleavage, while cleaved mixtures were not separated in native condition. Native digested sample mixtures without heating and denatured samples with heating in water bath were loaded on the same SDS-PAGE for verifying whether two fragments were stick together. The results showed that the native samples have only a single band with green fluorescence while denatured samples have two bands with molecular weight of 20 kDa and 8 kDa on SDS-PAGE, as shown in FIGS. 11 and 12. The band of 20 kDa showed similar yellow color with modified EGFP in SDS-PAGE before Coomassie blue staining. This result shows that the P20 and P8 fragment are able to stick together so that they are difficult to be separated in native form, which is in agreement with above investigations of GFP fragment reconstitution for tracking protein-protein interactions and further confirmed that our mini-GFP can be used to study protein-protein interactions in vivo for tracking cellular events or determining protease activity through a specific signal peptide or linkers to target the host proteins in specific compartments.

Although the P20 and P8 are tendency to stick together and still maintain strong fluorescence after digestion, P20 can emits weak green fluorescence at 503 nm in neutral Tris buffer without the aid of P8. The P20 with 172 amino acids and 157 amino acids greatly decreased the requirement for fluorescence in minimal domain of amino acid 7-229 from other research achievements The foregoing detailed description of the preferred embodiments and the appended figures have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the scope and spirit of the invention.

What is claimed is:

1. An isolated polynucleotide comprising:
a nucleotide sequence encoding a fluorescent polypeptide which is at least 90% sequence identical to a polypeptide selected from the group consisting of the polypeptide of SEQ ID NOs.: 9, 10, 11, 12, 13, 14, 15, and 16, and wherein the polypeptide includes a trypsin cleavage site and the amino acid sequence GLu-GLu-Isoleu-Arg obtained therefrom.

2. The isolated polynucleotide of claim 1, wherein the encoded fluorescent protein has between 178 and 184 amino acids.

3. The isolated polynucleotide of claim 1, wherein the nucleic acid sequence also encodes a polypeptide of interest.

4. The polynucleotide according to claim 1, wherein the fluorescent protein has an emission peak at about 500 nm.

5. The isolated polynucleotide of claim 1, wherein polynucleotide is capable of expressing as a polypeptide with mass of about 20361 to 20864 Daltons.

6. The polynucleotide according to claim 1, wherein the fluorescent protein has an absorbance band of about 469 nm to about 483 nm.

7. The polynucleotide according to claim 1, wherein the polynucleotide encodes a fluorescent protein capable of interacting with a smaller protein which is at least 85% sequence identical to the polypeptide of SEQ. ID. NO. 4, wherein the interaction of the smaller protein and the fluorescent protein produces a fluorescent signal that is different from the fluorescent protein fluorescent signal.

8. A vector comprising the polynucleotide of claim 1.

9. A host cell comprising the vector of claim 1.

10. An expression vector comprising suitable expression control sequences operatively linked to the nucleic acid molecule of claim 1.

11. A host cell transformed or transfected with a DNA construct comprising the expression vector of claim 10.

12. The host cell of claim 11, wherein said host cell is selected from the group consisting of mammalian cells, bacterial cells, yeast cells and insect cells.

13. A method for preparing a fluorescent protein comprising cultivating the host cell of claim 9.

14. The polynucleotide according to claim 1, wherein the fluorescent polypeptide is at least 95% sequence identical to a polypeptide selected from the group consisting of the polypeptide of SEQ ID NOs.: 9, 10, 11, 12, 13, 14, 15, and 16.

15. The polynucleotide according to claim 1, wherein the fluorescent polypeptide is at least 97% sequence identical to a polypeptide selected from the group consisting of the polypeptide of SEQ ID NOs.: 9, 10, 11, 12, 13, 14, 15, and 16.

16. The polynucleotide according to claim 1, wherein the polypeptide is identical to a polypeptide selected from the group consisting of the polypeptide of SEQ ID NOs.: 9, 10, 11, 12, 13, 14, 15, and 16.

* * * * *

SEQUENCE LISTING

```
<160> NUMBER OF SEQ ID NOS: 23

<210> SEQ ID NO 1
<211> LENGTH: 270
<212> TYPE: PRT
<213> ORGANISM: Artificial Sequence
<220> FEATURE:
<223> OTHER INFORMATION: Chemically modified green fluorescent protein
      from Aequorea

<400> SEQUENCE: 1

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
                180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
        210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 2
<211> LENGTH: 270
<212> TYPE: PRT
<213> ORGANISM: Artificial Sequence
<220> FEATURE:
<223> OTHER INFORMATION: Chemically modified green fluorescent protein
      from Aequorea

<400> SEQUENCE: 2

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Glu Glu
145                 150                 155                 160

Glu Ile Arg Glu Ala Phe Arg Val Phe Asp Lys Asp Gly Asn Gly Tyr
                165                 170                 175

Ile Ser Ala Ala Glu Leu Arg His Val Met Thr Asn Leu Lys Asn Gly
                180                 185                 190

Ile Lys Val Asn Phe Lys Ile Arg His Asn Ile Glu Asp Gly Ser Val
                195                 200                 205
```

```
Gln Leu Ala Asp His Tyr Gln Gln Asn Thr Pro Ile Gly Asp Gly Pro
        210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 3
<211> LENGTH: 270
<212> TYPE: PRT
<213> ORGANISM: Artificial Sequence
<220> FEATURE:
<223> OTHER INFORMATION: Chemically modified yellow fluorescent protien
      derived from a modified green fluorescent protein from Aequorea

<400> SEQUENCE: 3

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
        210                 215                 220

Val Leu Leu Pro Asp Asn His Tyr Leu Ser Tyr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
                260                 265                 270

<210> SEQ ID NO 4
<211> LENGTH: 270
<212> TYPE: PRT
<213> ORGANISM: Artificial Sequence
<220> FEATURE:
```

-continued

<223> OTHER INFORMATION: Chemically modified yellow fluorescent protien
derived from a modified green fluorescent protein from Aequorea

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Gly Tyr Gly Leu Gln Cys Ala Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Glu Glu
145                 150                 155                 160

Gly Ile Arg Glu Ala Phe Arg Val Phe Asp Lys Asp Gly Asn Gly Tyr
                165                 170                 175

Ile Ser Ala Ala Glu Leu Arg His Val Met Thr Asn Leu Lys Asn Gly
            180                 185                 190

Ile Lys Val Asn Phe Lys Ile Arg His Asn Ile Glu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Tyr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270
```

<210> SEQ ID NO 5
<211> LENGTH: 270
<212> TYPE: PRT
<213> ORGANISM: Artificial Sequence
<220> FEATURE:
<223> OTHER INFORMATION: Chemically modified cyano fluorescent protien
derived from a modified green fluorescent protein from Aequorea

<400> SEQUENCE: 5

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Ser Trp Gly Val Gln Cys Phe Ser Arg Tyr Pro Asp His Met Lys
```

```
                65                  70                  75                  80
Gln His Asp Phe Phe Lys Ser Ala Met Pro Glu Gly Tyr Val Gln Glu
                    85                  90                  95

Arg Thr Ile Phe Phe Lys Asp Asp Gly Asn Tyr Lys Thr Arg Ala Glu
                    100                 105                 110

Val Lys Phe Glu Gly Asp Thr Leu Val Asn Arg Ile Glu Leu Lys Gly
                    115                 120                 125

Ile Asp Phe Lys Glu Asp Gly Asn Ile Leu Gly His Lys Leu Glu Tyr
                    130                 135                 140

Ile Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu
                    165                 170                 175

Ile Arg Glu Ala Phe Arg Val Phe Asp Lys Asp Gly Asn Gly Tyr Ile
                    180                 185                 190

Ser Ala Ala Glu Leu Arg His Val Met Thr Asn Leu Asp Gly Ser Val
                    195                 200                 205

Gln Leu Ala Asp His Tyr Gln Gln Asn Thr Pro Ile Gly Asp Gly Pro
                    210                 215                 220

Val Leu Leu Pro Asp Asn His Tyr Leu Ser Thr Gln Ser Ala Leu Ser
225                 230                 235                 240

Lys Asp Pro Lys Glu Lys Arg Asp His Ile Val Leu Leu Glu Phe Val
                    245                 250                 255

Thr Ala Ala Gly Ile Thr Leu Gly Met Asp Glu Leu Tyr Lys
                    260                 265                 270

<210> SEQ ID NO 6
<211> LENGTH: 270
<212> TYPE: PRT
<213> ORGANISM: Artificial Sequence
<220> FEATURE:
<223> OTHER INFORMATION: Chemically modified cyano fluorescent protien
      derived from a modified green fluorescent protein from Aequorea

<400> SEQUENCE: 6

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                    20                  25                  30

Glu Gly Glu Gly Asp Ala Thr Tyr Gly Lys Leu Thr Leu Lys Phe Ile
                    35                  40                  45

Cys Thr Thr Gly Lys Leu Pro Val Pro Trp Pro Thr Leu Val Thr Thr
        50                  55                  60

Leu Ser Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                    85                  90                  95

Arg Thr Ile Phe Phe Lys Asp Asp Gly Asn Tyr Lys Thr Arg Ala Glu
                    100                 105                 110

Val Lys Phe Glu Gly Asp Thr Leu Val Asn Arg Ile Glu Leu Lys Gly
                    115                 120                 125

Ile Asp Phe Lys Glu Asp Gly Asn Ile Leu Gly His Lys Leu Glu Tyr
                    130                 135                 140

Ile Tyr Asn Ser His Asn Val Tyr Ile Thr Ala Asp Lys Gln Glu Glu
145                 150                 155                 160

Glu Ile Arg Glu Ala Phe Arg Val Phe Asp Lys Asp Gly Asn Gly Tyr
```

```
            165                 170                 175
Ile Ser Ala Ala Glu Leu Arg His Val Met Thr Asn Leu Lys Asn Gly
            180                 185                 190

Ile Lys Ala Asn Phe Lys Ile Arg His Asn Ile Glu Asp Gly Ser Val
            195                 200                 205

Gln Leu Ala Asp His Tyr Gln Gln Asn Thr Pro Ile Gly Asp Gly Pro
            210                 215                 220

Val Leu Leu Pro Asp Asn His Tyr Leu Ser Thr Gln Ser Ala Leu Ser
225                 230                 235                 240

Lys Asp Pro Lys Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 7
<211> LENGTH: 270
<212> TYPE: PRT
<213> ORGANISM: Artificial Sequence
<220> FEATURE:
<223> OTHER INFORMATION: Chemically modified blue fluorescent protien
      derived from a modified green fluorescent protein from Aequorea

<400> SEQUENCE: 7

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Phe
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg Glu Ala Phe Arg Val Phe Asp Lys Asp Gly Asn Gly Tyr Ile
            180                 185                 190

Ser Ala Ala Glu Leu Arg His Val Met Thr Asn Leu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
```

<210> SEQ ID NO 8
<211> LENGTH: 270
<212> TYPE: PRT
<213> ORGANISM: Artificial Sequence
<220> FEATURE:
<223> OTHER INFORMATION: Chemically modified blue fluorescent protien derived from a modified green fluorescent protein from Aequorea

<400> SEQUENCE: 8

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Ser His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Phe
130                 135                 140

Asn Tyr Asn Ser His Asn Val Tyr Ile Met Ala Asp Lys Gln Glu Glu
145                 150                 155                 160

Glu Ile Arg Glu Ala Phe Arg Val Phe Asp Lys Asp Gly Asn Gly Tyr
                165                 170                 175

Ile Ser Ala Ala Glu Leu Arg His Val Met Thr Asn Leu Lys Asn Gly
            180                 185                 190

Ile Lys Val Asn Phe Lys Ile Arg His Asn Ile Glu Asp Gly Ser Val
        195                 200                 205

Gln Leu Ala Asp His Tyr Gln Gln Asn Thr Pro Ile Gly Asp Gly Pro
210                 215                 220

Val Leu Leu Pro Asp Asn His Tyr Leu Ser Thr Gln Ser Ala Leu Ser
225                 230                 235                 240

Lys Asp Pro Asn Glu Lys Arg Asp His Ile Val Leu Leu Glu Phe Val
                245                 250                 255

Thr Ala Ala Gly Ile Thr Leu Gly Met Asp Glu Leu Tyr Lys
            260                 265                 270
```

<210> SEQ ID NO 9
<211> LENGTH: 270
<212> TYPE: PRT
<213> ORGANISM: Artificial Sequence
<220> FEATURE:
<223> OTHER INFORMATION: Chemically synthesized fluorescent protein

<400> SEQUENCE: 9

```
Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30
```

```
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
 50                  55                  60
Leu Ser His Gly Val Gln Cys Phe Ser Arg Tyr Pro Asp His Met Lys
 65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
            115                 120                 125
Ile Asp Phe Lys Glu Asp Gly Asn Ile Leu Gly His Lys Leu Glu Phe
130                 135                 140
Asn Tyr Asn Ser His Asn Val Tyr Ile Met Ala Asp Lys Gln Glu Glu
145                 150                 155                 160
Glu Ile Arg Glu Ala Phe Arg Val Phe Asp Lys Asp Gly Asn Gly Tyr
                165                 170                 175
Ile Ser Ala Ala Glu Leu Arg His Val Met Thr Asn Leu Lys Asn Gly
            180                 185                 190
Ile Lys Val Asn Phe Lys Ile Arg His Asn Ile Glu Asp Gly Ser Val
            195                 200                 205
Gln Leu Ala Asp His Tyr Gln Gln Asn Thr Pro Ile Gly Asp Gly Pro
210                 215                 220
Val Leu Leu Pro Asp Asn His Tyr Leu Ser Thr Gln Ser Ala Leu Ser
225                 230                 235                 240
Lys Asp Pro Asn Glu Lys Arg Asp His Ile Val Leu Leu Glu Phe Val
                245                 250                 255
Thr Ala Ala Gly Ile Thr Leu Gly Met Asp Glu Leu Tyr Lys
                260                 265                 270

<210> SEQ ID NO 10
<211> LENGTH: 163
<212> TYPE: PRT
<213> ORGANISM: Artificial Sequence
<220> FEATURE:
<223> OTHER INFORMATION: Chemically synthesized fluorescent protein

<400> SEQUENCE: 10

Met Val Ser Lys Gly Glu Glu Leu Phe Thr Gly Val Val Pro Ile Leu
 1               5                  10                  15
Val Glu Leu Asp Gly Asp Leu Asn Gly His Lys Phe Ser Val Ser Gly
                20                  25                  30
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
 50                  55                  60
Leu Thr Tyr Gly Val Gln Cys Phe Ser Arg Tyr Pro Asp His Met Lys
 65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
            115                 120                 125
Ile Asp Phe Lys Glu Asp Gly Asn Ile Leu Gly His Lys Leu Glu Tyr
```

```
                130                 135                 140
Asn Tyr Asn Ser His Asn Val Tyr Ile Met Ala Asp Lys Gln Glu Glu
145                 150                 155                 160

Glu Ile Arg

<210> SEQ ID NO 11
<211> LENGTH: 177
<212> TYPE: PRT
<213> ORGANISM: Artificial Sequence
<220> FEATURE:
<223> OTHER INFORMATION: Chemically synthesized fluorescent protein

<400> SEQUENCE: 11

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu
                165                 170                 175

Ile

<210> SEQ ID NO 12
<211> LENGTH: 178
<212> TYPE: PRT
<213> ORGANISM: Artificial Sequence
<220> FEATURE:
<223> OTHER INFORMATION: Chemically synthesized fluorescent protein

<400> SEQUENCE: 12

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Ser Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Ile Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Glu Glu Glu
                165                 170                 175

Ile Arg

<210> SEQ ID NO 13
<211> LENGTH: 178
<212> TYPE: PRT
<213> ORGANISM: Artificial Sequence
<220> FEATURE:
<223> OTHER INFORMATION: Chemically synthesized fluorescent protein

<400> SEQUENCE: 13

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Ser His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Phe
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Glu Glu Glu
                165                 170                 175

Ile Arg

<210> SEQ ID NO 14
<211> LENGTH: 163
<212> TYPE: PRT
<213> ORGANISM: Artificial Sequence
<220> FEATURE:
<223> OTHER INFORMATION: Chemically synthesized fluorescent protein

<400> SEQUENCE: 14

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45
```

```
Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65              70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Glu Glu
145                 150                 155                 160

Glu Ile Arg

<210> SEQ ID NO 15
<211> LENGTH: 162
<212> TYPE: PRT
<213> ORGANISM: Artificial Sequence
<220> FEATURE:
<223> OTHER INFORMATION: Chemically synthesized fluorescent protein

<400> SEQUENCE: 15

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Gly Tyr Gly Leu Gln Cys Ala Ser Arg Tyr Pro Asp His Met Lys
65              70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Glu Glu
145                 150                 155                 160

Ile Arg

<210> SEQ ID NO 16
<211> LENGTH: 163
<212> TYPE: PRT
<213> ORGANISM: Artificial Sequence
<220> FEATURE:
<223> OTHER INFORMATION: Chemically synthesized fluorescent protein

<400> SEQUENCE: 16

Met Val Ser Lys Gly Glu Glu Leu Phe Thr Gly Val Val Pro Ile Leu
1               5                   10                  15

Val Glu Leu Asp Gly Asp Leu Asn Gly His Lys Phe Ser Val Ser Gly
```

```
                    20                  25                  30
Glu Gly Glu Gly Asp Ala Thr Tyr Gly Lys Leu Thr Leu Lys Phe Ile
            35                  40                  45
Cys Thr Thr Gly Lys Leu Pro Val Pro Trp Pro Thr Leu Val Thr Thr
    50                  55                  60
Leu Ser Trp Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140
Ile Tyr Asn Ser His Asn Val Tyr Ile Thr Ala Asp Lys Gln Glu Glu
145                 150                 155                 160
Glu Ile Arg

<210> SEQ ID NO 17
<211> LENGTH: 163
<212> TYPE: PRT
<213> ORGANISM: Artificial Sequence
<220> FEATURE:
<223> OTHER INFORMATION: Chemically synthesized fluorescent protein

<400> SEQUENCE: 17

Met Val Ser Lys Gly Glu Glu Leu Phe Thr Gly Val Val Pro Ile Leu
1               5                   10                  15
Val Glu Leu Asp Gly Asp Leu Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
    50                  55                  60
Leu Ser His Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Phe
    130                 135                 140
Asn Tyr Asn Ser His Asn Val Tyr Ile Met Ala Asp Lys Gln Glu Glu
145                 150                 155                 160
Glu Ile Arg

<210> SEQ ID NO 18
<211> LENGTH: 72
<212> TYPE: PRT
<213> ORGANISM: Artificial Sequence
<220> FEATURE:
<223> OTHER INFORMATION: Chemically synthesized protein fragment able to
      complex with a fluorescent protein

<400> SEQUENCE: 18
```

```
His Val Met Thr Asn Leu Asp Gly Ser Val Gln Leu Ala Asp His Tyr
1               5                   10                  15

Gln Gln Asn Thr Pro Ile Gly Asp Gly Pro Val Leu Leu Pro Asp Asn
                20                  25                  30

His Tyr Leu Ser Thr Gln Ser Ala Leu Ser Lys Asp Pro Asn Glu Lys
            35                  40                  45

Arg Asp His Ile Val Leu Leu Glu Phe Val Thr Ala Ala Gly Ile Thr
        50                  55                  60

Leu Gly Met Asp Glu Leu Tyr Lys
65                  70
```

```
<210> SEQ ID NO 19
<211> LENGTH: 87
<212> TYPE: PRT
<213> ORGANISM: Artificial Sequence
<220> FEATURE:
<223> OTHER INFORMATION: Chemically synthesized protein fragment able to
      complex with a fluorescent protein

<400> SEQUENCE: 19
```

```
His Val Met Thr Asn Leu Lys Asn Gly Ile Lys Val Asn Phe Lys Ile
1               5                   10                  15

Arg His Asn Ile Glu Asp Gly Ser Val Gln Leu Ala Asp His Tyr Gln
                20                  25                  30

Gln Asn Thr Pro Ile Gly Asp Gly Pro Val Leu Leu Pro Asp Asn His
            35                  40                  45

Tyr Leu Ser Thr Gln Ser Ala Leu Ser Lys Asp Pro Asn Glu Lys Arg
        50                  55                  60

Asp His Ile Val Leu Leu Glu Phe Val Thr Ala Ala Gly Ile Thr Leu
65                  70                  75                  80

Gly Met Asp Glu Leu Tyr Lys
                85
```

```
<210> SEQ ID NO 20
<211> LENGTH: 31
<212> TYPE: PRT
<213> ORGANISM: Artificial Sequence
<220> FEATURE:
<223> OTHER INFORMATION: Chemically synthesized peptide including a
      cleavage site

<400> SEQUENCE: 20
```

```
Glu Glu Glu Ile Arg Glu Ala Phe Arg Val Phe Asp Lys Asp Gly Asn
1               5                   10                  15

Gly Tyr Ile Ser Ala Ala Glu Leu Arg His Val Met Thr Asn Leu
            20                  25                  30
```

```
<210> SEQ ID NO 21
<211> LENGTH: 4
<212> TYPE: PRT
<213> ORGANISM: Artificial Sequence
<220> FEATURE:
<223> OTHER INFORMATION: Localization Sequence

<400> SEQUENCE: 21
```

```
Lys Lys Arg Lys
1
```

```
<210> SEQ ID NO 22
<211> LENGTH: 26
<212> TYPE: PRT
<213> ORGANISM: Artificial Sequence
```

```
<220> FEATURE:
<223> OTHER INFORMATION: Localization Sequence

<400> SEQUENCE: 22

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 23
<211> LENGTH: 16
<212> TYPE: PRT
<213> ORGANISM: Artificial Sequence
<220> FEATURE:
<223> OTHER INFORMATION: Localization Sequence

<400> SEQUENCE: 23

Met Leu Leu Ser Val Pro Leu Leu Gly Leu Leu Gly Leu Ala Ala Asp
1               5                   10                  15
```